United States Patent [19]

Grim et al.

[11] Patent Number: 4,869,267
[45] Date of Patent: Sep. 26, 1989

[54] ADJUSTABLE TENSION ANKLE SUPPORT

[75] Inventors: Tracy E. Grim, Broken Arrow, Okla.; Thomas M. Smario, Portland, Oreg.

[73] Assignee: Royce Medical Company, Westlake Village, Calif.

[21] Appl. No.: 192,461

[22] Filed: May 10, 1988

[51] Int. Cl.$^4$ ............................................... A61F 5/00
[52] U.S. Cl. .................................... 128/80 H; 128/166
[58] Field of Search ................... 128/80 H, 166, 80 J, 128/80 R, 80 C

[56] References Cited

U.S. PATENT DOCUMENTS

| | | | |
|---|---|---|---|
| 5,393 | 12/1847 | Chamberlin | 128/80 J |
| 1,037,441 | 9/1912 | Collis | 128/166 |
| 1,040,279 | 10/1912 | Collis | 128/166 |
| 1,656,322 | 1/1928 | Fischer | 128/80 J |
| 2,592,739 | 4/1952 | Richardson | 128/166 |
| 3,073,305 | 1/1963 | Biggs | 128/80 H |
| 3,306,610 | 2/1967 | Biggs | 128/166 |
| 3,674,023 | 7/1972 | Mann | 128/166 |
| 4,217,893 | 8/1980 | Payton | 128/165 |
| 4,313,433 | 2/1982 | Cramer | 128/80 H |
| 4,323,058 | 4/1982 | Detty | 128/166 |
| 4,414,965 | 11/1983 | Mauldin et al. | 128/166 |
| 4,440,158 | 4/1984 | Shapiro | 128/80 H |
| 4,527,556 | 7/1985 | Nelson | 128/166 |
| 4,547,981 | 10/1985 | Thais | 128/166 |
| 4,573,482 | 3/1986 | Williams | 128/80 R |
| 4,577,419 | 3/1986 | Chassaing | 128/166 |
| 4,621,648 | 11/1986 | Ivany | 128/80 H |
| 4,724,847 | 2/1988 | Nelson | 128/80 H |

*Primary Examiner*—William Pieprz
*Assistant Examiner*—Huong Q. Pham
*Attorney, Agent, or Firm*—Poms, Smith, Lande & Rose

[57] ABSTRACT

An ankle brace includes an outer supporting casing for enclosing the ankle, and two side cruciate elastic straps, each having one end secured within the supporting casing near the sole of the user's foot, with the straps extended across the instep or the front of the ankle and across one-another in a cruciate configuration. Tensioning lines are secured to the free ends of each of the straps and extend through eyelets on each side of the front of the supporting casing, ending in D-rings, through which shoelaces may be tied to tension the cruciate straps.

21 Claims, 2 Drawing Sheets

U.S. Patent  Sep. 26, 1989  Sheet 1 of 2  4,869,267

ADJUSTABLE TENSION ANKLE SUPPORT

FIELD OF THE INVENTION

This invention relates to soft-goods type ankle braces or supports.

BACKGROUND OF THE INVENTION

Many different types of ankle braces or supports have been proposed heretofore. One such prior type of brace is disclosed in U.S. Patent Application Ser. No. 055,711 filed May 29, 1987, assigned to the assignee of this application, and in certain patents cited therein, including D. M. Mauldin, et al., U.S. Pat. No. 4,572,169, granted Feb. 25, 1986, and G. E. Detty U.S. Pat. No. 4,323,058 granted Apr. 6, 1982. However, the type of brace shown in the Mauldin patent is relatively massive and complex, and is intended for use with major medical problems. On the other hand, most of the soft goods type ankle supports, such as that shown by Detty and those available on the market are either so flimsy as to provide little support, or are of cumbersome and impractical mechanical designs.

Accordingly, principal objects of the present invention are to provide a soft goods type ankle support, which is relatively simple to put on and take off, includes adjustable tension, and which provides strong ankle support through a sound mechanical design.

SUMMARY OF THE INVENTION

In accordance with the present invention, a soft goods type ankle support includes an outer flexible supporting casing enclosing the ankle and extending around the forefoot and the dorsal aspect or front of the ankle, and first and second wide cruciate elastic straps, each having one end secured to respectively different sides of the outer casing within the casing and along a line near the location of the sole of the user's foot, and with the straps extending across one another in a cruciate configuration and across the front of the ankle. A tensioning line or lace is secured to the free end of each of the cruciate straps, and these lines extend through eyelets on respectively different sides of the front of the supporting casing. The tensioning lines have loops, such as D-rings, secured to their outer ends for receiving shoelaces to apply tension to the lines and firmly pull the cruciate elastic straps tightly across the front of the ankle.

The ankle brace or support may include additional features, such as any one or more of the following:

1. The outer supporting casing may have a zipper up one side of the rear thereof to facilitate putting the support on or taking it off.

2. The front of the supporting casing may be open and have VELCRO (hook and loop material) straps secured to first side, extending through rectangular or oval eyelets on the other side and back to mating VELCRO (hook and loop material) pads on the first side, to secure the front closed.

3. An elastic strip or tape may extend along the bottom of the supporting casing, securing the two halves of the casing together to accommodate feet of different widths.

4. An inner wide felt tongue may extend up the front of the assembly to pad the front of the foot and ankle.

5. An inner elastic tube-like liner may be provided, extending from the top of the outer supporting casing to the other end thereof, and having two edges at the upper rear thereof secured to said supporting casing at opposite sides of the zipper.

6. The laces of an athletic shoe or the like, put on after the ankle support is in place, may be tied through the outer rings secured to the tensioning lines, to apply the desired tension to the cruciate elastic straps.

7. The support casing may be formed of canvas for durability and "breathability".

8. The rings secured to the tensioning lines or laces should be larger than the eyelets through which the lines extend, so that the rings are readily available for securing to shoelaces.

9. The heel and the toe of the user are exposed after the ankle support is in place.

Other objects, features, and advantages of the invention will become apparent from a consideration from the following detailed description and from the accompanying drawings.

DETAILED DESCRIPTION

Figure 1:
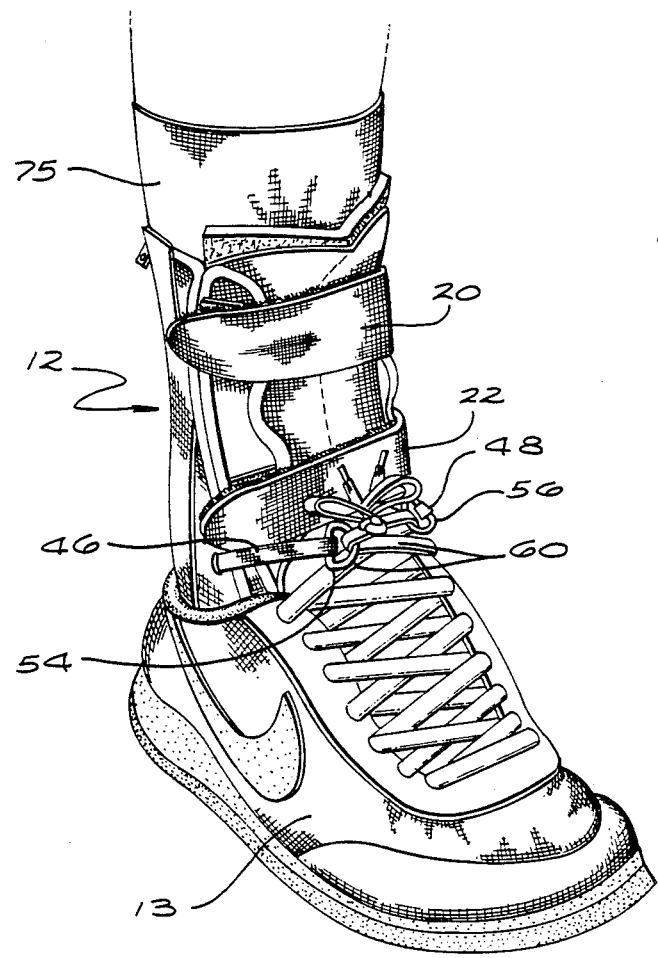
FIG. 1 is a perspective view of an ankle brace or support, illustrating the principles of the invention, in combination with an athletic shoe.
Figure 2:
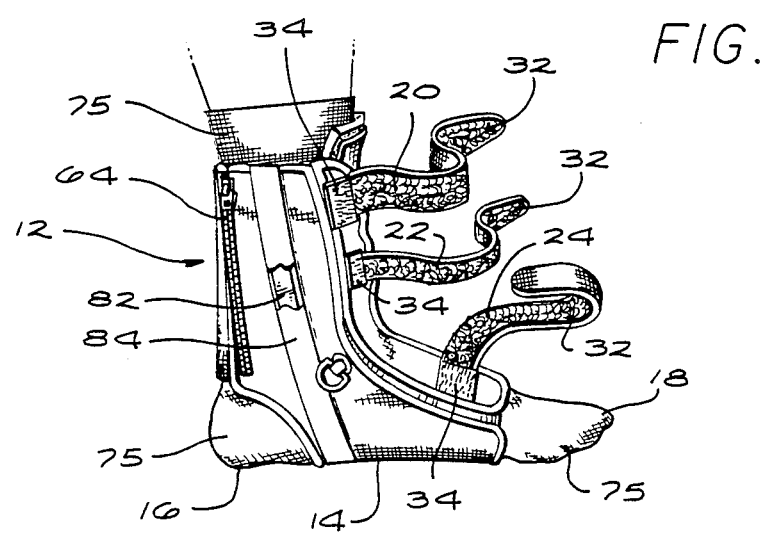
FIG. 2 shows the ankle support assembly illustrating the principles of the invention with the shoe removed and the straps loosened.
Figure 3:
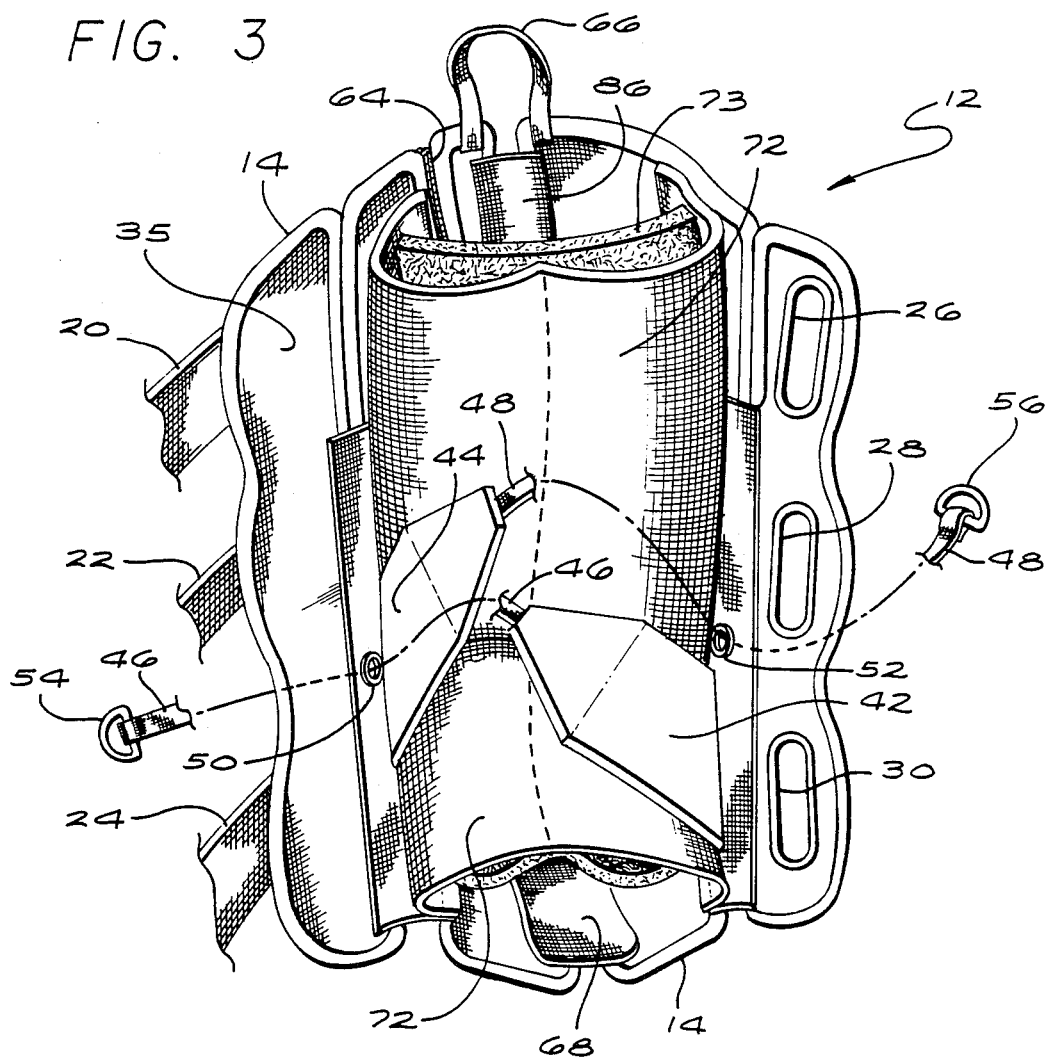
FIG. 3 is a view from the front of the ankle support assembly showing its inner construction.

Referring more particularly to the drawings, FIG. 1 shows an ankle support assembly illustrating the principles of the present invention at reference numeral 12, and an athletic shoe 13 which is being worn over the ankle support assembly. The assembly 12, as shown in FIGS. 1 through 5, include an outer canvas support casing 14 which generally encloses the ankle and the foot, leaving the heel 16 and toe 18 of the user open. The outer supporting casing is open at the front, and has three straps 20, 22 and 24 which serve to adjustably hold the open front of the support casing closed. As best seen in FIG. 3 of the drawings, the straps 20, 22 and 24 are secured to one side of the open front of the support casing, and are threaded through the moderately large rectangular or oval eyelets 26, 28 and 30 on the opposite front edge of the support casing 14. As shown in FIG. 2, the canvas, straps 20, 22 and 24, have one type of VELCRO material, such as hooked material 32 on their outer ends, which fold back and mate with the loop type VELCRO pad material 34, which is secured to the base of the straps, or to the support casing 14. The canvas support casing 14 has a lining 35 of soft finely woven material extending over its inner surface.

Now, referring to FIG. 3, an important aspect of the invention involves the two cruciate straps 42 and 44. They are secured to the support casing close to the location of the sole of the user's foot, and extend up across the inside of the ankle and forefoot, crossing one another, and are secured to the tensioning lines or webs 46 and 48, respectively. The D-rings 54 and 56 are of such a size that they will not fit through the openings or eyelets 50 or 52. These tensioning lines or webbing 46 and 48 extend through the eyelets 50 and 52, respectively, and the D-rings 54 and 56 are firmly secured to the ends of the tensioning lines 46 and 48, respectively. As shown in FIG. 1, the laces 60 are brought through the D-rings 54 and 56 as the shoelaces are being tied together, and by putting the proper tension on the shoelaces, and pulling the D-rings and associated tensioning lines tight, the cruciate straps 42 and 44 may be drawn across the instep or inner portion of the ankle, to tighten the brace assembly to the degree desired or required by the user.

Figure 4:
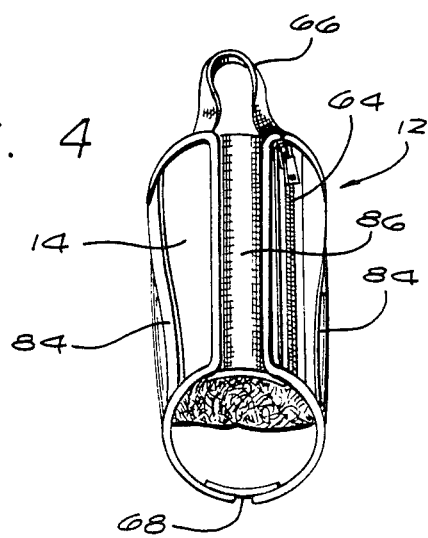
FIG. 4 is a rear view of the ankle support assembly.
Figure 5:
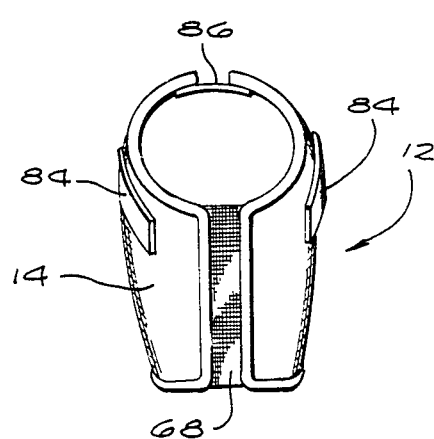
FIG. 5 is a front and bottom view of the ankle support unit.

The zipper 64, as shown in FIGS. 2 and 4 of the drawings, is lowered, to release the two halves of the support casing, when it is desired to put the ankle brace on, or take if off. The strap 66, as shown in FIGS. 3 and 4, is helpful in pulling the unit onto the foot.

Elastic stockingette type material is formed into two-thirds or three-quarters of a sleeve 72, and secured to the support casing 14, along the side of the user's foot, and near the rear of the user's ankle, at each side. The felt tongue or strip 73 is secured to the sleeve 72 and extends up the front of the sleeve to pad the instep or the front of the ankle. Joining two halves of the support casing 14 under the instep, is a strip of elastic material 68, to accommodate feet of different widths.

Incidentally, in FIGS. 1 and 2, it may be noted that the user is wearing a stocking or sock 75 within the ankle support assembly illustrating the present invention.

Concerning materials, it was noted that the outer support casing 14 may be formed of canvas material, which has the advantage of being only moderately flexible, and being porous. The material 72 is preferably made of material which will stretch in two directions; and the elastic straps 42 may be formed of material which will only stretch the longitudinal direction along the longitudinal axes of the straps. The tensioning lines or webbing elements 46 and 48 preferably are non-elastic, and could be made of materials similar to that from which shoelaces are formed. The eyelets 50, 52, and 26, 28 and 30, are formed of metal, and may be crimped over on both sides of the canvas material, as is conventional for eyelets.

Shown in FIG. 2 is an aluminum stay 82, mounted in a pocket 84 which extends from the top to the bottom of the ankle support assembly. A similar stay is located on the other side of the assembly to provide desired lateral support for the ankle. An additional elastic strip 86 joins the two rear edges of the support casing 14, to complete the enclosure.

It is to be understood that the foregoing detailed description and the accompanying drawings relate to one illustrative embodiment of the invention. Various changes and alterations may be made without departing from the spirit and scope of the invention. Thus, by way of example and not of limitation, the cruciate elastic straps and their associated tie lies may be employed with other forms of ankle braces than the specific ones shown in the present drawings. In addition, the cruciate elastic straps may have additional non-elastic straps secured to their free ends, and these additional straps may be adjustably tensioned by mating VELCRO (hook and loop material) and outer support casing. Further, the two sides of the front of the support assembly may be held together by arrangements other than the straps 20, 22 and 24, such as by direct overlapping of mating VELCRO (hook and loop material) surfaces, Accordingly, the present invention is not limited to the arrangements precisely as shown in the drawings and as described in the detailed description.

What is claimed is:

1. A soft goods type ankle brace or support with adjustable tension for use within a shoe having shoelaces, comprising:

an inelastic flexible outer supporting casing having a shape generally conforming to the ankle and foot, with the heel open, and extending from above the ankle and enclosing the foot including the instep, but stopping short of the toes;

said outer supporting casing having an upper edge at the top thereof, a rear portion for location behind the ankle of the user and a front portion for extending down the front of the ankle and over the instep of the foot of the user to a front end of said supporting casing;

zipper closure means extending along one side of the rear of said outer supporting covering from the upper edge thereof, to permit opening of the rear of said outer supporting casing, said zipper closure means having two opposite sides, an inner tube of elastic material extending substantially from the top of said outer supporting casing to the front end thereof and having two edges secured to said outer casing at the rear thereof on opposite sides of said zipper closure means and forward along the sides of the user,s foot;

the front of said outer casing being open, having two front edges, and having at least three large rectangular or oval eyelets spaced along one front edge thereof, and first and second small eyelets spaced back from each front edge thereof, and located about halfway along the front edges of said outer supporting casing;

two wide cruciate elastic straps each having two ends with one end secured to said outer casing at a zone near the location of the sole of the user's foot and said straps extending across one another in a cruciate configuration and across the forefoot and the front of the ankle;

first and second non-elastic tensioning lines secured to the other ends of each of said cruciate straps and extending, respectively, through said first and second small eyelets;

rings secured to the outer ends of tensioning lines for engagement by shoelaces to adjust the tension on said elastic cruciate straps; and strap means extending from one side of the front of said supporting casing through said rectangular or oval eyelets and back into secure engagement with said one side of said supporting covering.

2. An ankle brace or support as defined in claim 1 further comprising VELCRO means for holding said strap means into engagement.

3. An ankle brace or support as defined in claim 1 wherein said casing is formed in two parts, a left part and a right part, and an elastic strap secures said two parts together along the sole of the user's foot.

4. An ankle brace or support as defined in claim 1 wherein said casing is formed in two parts, a left part and a right part, and an elastic strap secures said two parts together along the back thereof where it extends up the back of the user's ankle.

5. An assembly as defined in claim 1 further comprising a shoe having laces, and said laces extending through said rings and placing said lines under tension.

6. An ankle brace or support as defined in claim 1 wherein said rings are D-shaped in configuration, and of a size greater than the eyelet openings, so that the rings are always available outside the supporting casing for tightening the tensioning lines.

7. An assembly as defined in claim 1 further comprising stays extending from the top to the bottom of said supporting casing on both sides of the ankle of the user.

8. A soft goods ankle brace or support comprising:
outer supporting means having inner and outer sides for enclosing the user's ankle and adjacent portion of the foot;
means for adjusting the tightness of said outer supporting means on the user's ankle and foot;
two wide cruciate elastic straps within said supporting means and each having two ends with one end secured to said outer supporting means on the inner side thereof adjacent the sole of the user's foot, and extending upwardly across the forefoot and the inner portion of the ankle and across one-another in a cruciate configuration;
said supporting means having openings therethrough;
tensioning lines secured to the other ends of each of the cruciate straps and extending through the openings in said outer supporting means; and
means for applying tension to said tensioning lines independent of said adjusting means for said outer supporting means, to exert force on said elastic cruciate straps to firmly secure said ankle support onto the user's ankle.

9. An ankle brace or support as defined in claim 8 wherein said casing is formed in two parts, a left part and a right part, and an elastic strap secures said two parts together along the sole of the user's tool.

10. An ankle brace or support as defined in claim 8 wherein said casing is formed in two parts, a left part and a right part, and an elastic strap secures said two parts together along the back thereof where it extends up the back of the user's ankle.

11. An ankle brace or support as defined in claim 8 wherein said casing is formed in two parts, a left part and a right part, and strap means are provided for holding the front edges of said casing together.

12. An ankle brace or support as defined in claim 8 wherein said tensioning lines each having an inner and an outer end, with the inner ends being secured to said cruciate straps, and rings are secured to the outer ends of said tensioning lines, for engagement by shoelaces.

13. An ankle brace or support as defined in claim 8 wherein said outer supporting means has a rear portion for location behind the ankle of the user, and further comprising a zipper extending up one side of the rear portion of said outer supporting means.

14. An ankle brace or support as defined in claim 8 further comprising inner elastic material in a sleeve-like configuration secured to said casing along the side of the user's foot and near the rear of user's ankle to provide basic resilient continuing force to the user's ankle.

15. A soft goods ankle brace or support assembly comprising:
outer supporting means for enclosing the user's ankle;
two wide cruciate elastic straps each having one end secured to said outer supporting means adjacent the sole of the user's foot, and extending upwardly across the forefoot and the inner portion of the ankle and across one-another in a cruciate configuration;
said outer supporting means having openings therethrough and having an upper edge at the top thereof, a rear portion for location behind the ankle of the user and a front portion for extending down the front of the ankle and over the instep of the foot of the user to a front end of said supporting means;
tensioning lines secured to the other ends of each of the cruciate straps and extending through the openings in said outer supporting means;
means for applying tension to said tensioning lines to exert force on said elastic cruciate straps to firmly secure said ankle support onto the user's ankle;
a shoe having laces, said shoe being mounted over said outer supporting means; and
said laces being coupled to said tensioning lines to constitute the means for applying tension to said elastic cruciate straps.

16. An assembly as defined in claim 15 wherein said outer supporting means has a top intended for location above the ankle and a bottom intended for location at the sole of the foot of a user, and further comprising stays extending from the top to the bottom of said outer supporting means on both sides of the ankle of the user.

17. An ankle brace or support as defined in claim 15 wherein said outer supporting means has a rear portion for location behind the ankle of the user, and further comprising a zipper extending up one side of the rear portion of said outer supporting means.

18. An ankle brace or support as defined in claim 15 further comprising inner elastic material in a sleeve-like configuration, secured to said casing, along the side of the user's foot and near the rear of user's ankle to provide basic resilient force to the user's ankle.

19. An ankle brace or support as defined in claim 15 wherein said casing is formed in two parts, a left part and a right part, and an elastic strap secures said two parts together along the sole of the user's foot.

20. An ankle brace or support as defined in claim 15 wherein said casing is formed in two parts, a left part and a right part, and an elastic strap secures said two parts together along the back thereof where it extends up the back of the user's ankle.

21. A soft goods ankle brace or support comprising:
outer supporting means for enclosing the user's ankle;
two wide cruciate elastic straps within said supporting means and each having two ends, with one end secured to said outer supporting means adjacent the sole of the user's foot, and extending upwardly across the inner portion of the forefoot and ankle and across one-another in a cruciate configuration;
means secured to the other ends of each of the cruciate straps for selectively applying desired variable levels of tension to the other ends of said straps;
wherein said outer supporting means has openings therethrough, and said means for applying tension includes tensioning lines each having two ends with one end secured to the other end of a respective one of said straps, said tensioning lines extending through the openings of said supporting means.

* * * * *